United States Patent [19]
Klaue et al.

[11] Patent Number: 5,741,258
[45] Date of Patent: Apr. 21, 1998

[54] LOCK WASHER FOR BONE PLATE OSTEOSYNTHESIS

[75] Inventors: Kaj Klaue, Bern, Switzerland; Jeffrey W. Mast, Grosse Pointe Park, Mich.

[73] Assignee: Synthes (U.S.A.), Paoli, Pa.

[21] Appl. No.: 864,002

[22] Filed: May 27, 1997

Related U.S. Application Data

[63] Continuation of Ser. No. 302,968, filed as PCT/CH93/00018, Jan. 25, 1993, published as WO94/16634, Aug. 4, 1994, abandoned.

[51] Int. Cl.$^6$ .................................................. A61B 17/80
[52] U.S. Cl. .............................. 606/70; 606/69; 606/73
[58] Field of Search .................................. 606/69, 70, 71, 606/72, 73; 411/317, 314, 253, 324, 371, 427, 546

[56] References Cited

U.S. PATENT DOCUMENTS

| | | | |
|---|---|---|---|
| 4,373,309 | 2/1983 | Lutz | 411/427 X |
| 5,057,111 | 10/1991 | Park | 606/69 |
| 5,129,899 | 7/1992 | Small et al. | 606/61 |
| 5,167,532 | 12/1992 | Bruno et al. | 439/578 |
| 5,269,784 | 12/1993 | Mast | 606/69 |

FOREIGN PATENT DOCUMENTS

| | | |
|---|---|---|
| 0301489 | 2/1989 | European Pat. Off. |
| 0360139 | 3/1990 | European Pat. Off. |
| 0410309 | 1/1991 | European Pat. Off. |
| 0507162 | 10/1992 | European Pat. Off. |
| 3027148 | 12/1981 | Germany. |
| 3509417 | 9/1986 | Germany. |
| 9012547 | 11/1990 | WIPO. |

Primary Examiner—Guy V. Tucker
Attorney, Agent, or Firm—Fish & Richardson P.C.

[57] ABSTRACT

A lockwasher is provided for attaching a bone screw to a bone plate, thus making up an osteosynthetic system. The washer has a threaded screw hole, a lower section with a surface to be applied to a bone and an upper section shaped to be retained in a plate borehole, the lower section being of less than average width than the upper section.

16 Claims, 4 Drawing Sheets

LOCK WASHER FOR BONE PLATE OSTEOSYNTHESIS

This is a continuation of application Ser. No. 08/302,968, filed Sep. 12, 1994, now abandoned which is a 35 USC 371 application based on PCT/CH93/00018 filed on Jan. 25, 1993 published as WO94/16634, Aug. 4, 1994.

FIELD OF THE INVENTION

The invention concerns a lock washer for rigid fixation of bone screws to a bone plate as well as a fixation device with a lock washer of this type.

BACKGROUND OF THE INVENTION

Most bone plates employed in osteosynthesis are attached directly to the bone only by means of bone screws in the usual manner, and held onto the bone solely by the resulting friction force between the bone plate and bone. Since bone screws are simply anchored in the bone, no rigid fixation of the latter with the bone plate exists. Loosening of the screws in the bone or a resorption of the bone can thus easily lead to a loosening of the bone plate itself.

In bone plate osteosynthesis, bone plate screws are in fact known which pass completely through the bone to be secured by a nut on the end that is remote from the screw head. However, this method also does not effect any direct fixation between the screw and plate, but rather merely causes a compression of the bone lying between the nut and the plate and penetrated by the screw.

However, in a larger number of indications it is desirable to create a rigid fixation between the bone screw and bone plate, to avoid any subsequent loosening. For this purpose, it is already known from EP-A 340 223 that the head of the bone screw can be locked solely by frictional adhesion in a specially formed bone plate having conical boreholes. But with this known device special bone plates with boreholes having a selected taper, and special bone screws with screw heads configured to match, are required. A capacity of the bone screw to swivel is possible only with the help of additional costly measures, such as a separate spherical insert. A major insufficiency is that the fixation does not work if the plate is contoured.

It is likewise already known from EP-A 340 223 that the underside of the bone plate can be provided with raised portions, to reduce the contact surface adjoining the bone for the purpose of improving vascularity. The raised portions and the bone plate, however, form a single unit, which can only be used together and do not permit any individualized configurations. In addition the raised portions adjacent to the bone are positioned at the edge of the plate, i.e. at a substantial distance from the location where the bone screw passes through. The result of this is additional damage and encroachment on the bone surface.

SUMMARY OF THE INVENTION

For this problem, the invention will afford a remedy.

The invention provides a lock washer for bone plate osteosynthesis which can be used with any type of bone plate and bone screw, and optionally at any desired screw-hole in the bone plate. It simultaneously serves as a spacer to reduce the contact surface between the bone plate and the bone.

In accordance with the invention a lock washer is provided for attaching a bone screw to a bone plate, the washer comprising a substantially cylindrical body having a central axis, a borehole having internal threading for receiving a bone screw, a lower section adapted to abut the surface of a bone and an upper section, the upper section being shaped to be retained in a plate borehole and the lower section being smaller in average width than the upper section.

The invention further includes an osteosynthetic system comprising a bone plate having an upper surface, a lower surface for positioning to face a bone and a lock washer as described.

The upper portion of the lock washer according to the invention can be shaped in various ways, as long as it can be inserted into the hole of the bone plate. Preferably, however, an elliptical or roughly rectangular cross section profile will be selected so as to achieve a torsionally stable locking in the borehole of the bone plate. In addition, a locking connection is preferred between the upper section of the lock washer and the lower section of the borehole of the bone plate. It is more appropriate to set the dimensions of the axial height of the upper section so that it will have sufficient space to fit into the borehole of the bone plate.

The interior thread of the lock washer according to the invention must, of course, match the standardized exterior thread of the bone screw which is to be used.

In using the lock washer according to the invention with bone plates which also have circular boreholes, the lower section cannot be inserted in torsionally stable fashion, as with elliptical boreholes. To remedy this defect, the upper section of the lock washer, at minimum at the surface which adjoins the bone plate, is provided with a roughened surface or texture. A further improvement of torsional stability can be achieved by having the boreholes of the bone plate, at minimum at the surfaces which adjoin the lock washer, provided with a roughened surface or texture. Thanks to this or similar measures (i.e., corresponding raised surfaces and recesses in the two adjoining surfaces), rotational stability which is otherwise lacking may be attained.

The advantages of the lock washer according to the invention are evident primarily in its universal applicability, since it can be combined with practically any type of bone plate and bone screw. In addition, it permits an application specifically limited to individual holes of the bone plate and the bone screws inserted into it. Use of the lock washer according to the invention can thus be made intraoperatively in any operational phase.

A further advantage of the lock washer according to the invention is in its function as a spacer between the bone plate and the bone. The reduced contact surface permits improved blood flow and thus a speedier healing. In this regard, one feature of particular importance is that the surface where the bone is adjacent to the lock washer according to the invention is directly at the point where the bone screw passes through. Thus, on the one hand, there is a slightly increased encroachment on the bone surface in this area, which is already subjected to loading; and on the other hand, there is an increase in mechanical stability of the lock washer (serving as a spacer) in the contact area close to the bone.

In addition, owing to the rigid fixation of the bone screw to the bone plate by means of the lock washer, it is possible to place the bone plate at a defined distance from the bone, resulting in a so-called ultra-low profile external fixator.

Furthermore, the rigid fixation prevents undesired deformities, as can take place with axial compression upon rotation of the screw.

The locking disk also permits a certain degree of energy storage when compression is exerted on the fracture. Thus, it is possible to exert a longer-lasting compression effect.

This also removes the load on the screws that are positioned in the conventional way through a plate hole, as for example tension bolts or so-called plate tension bolts.

In addition, the lock washer allows a certain lateral tilt capacity of the bone screw relative to the central axis of the plate hole without requiring that additional accessories be provided.

Furthermore, the curvedly tapered, cylindrical lock washer implies the advantage that a firm fixation of the bone screw is given even if the bore hole in the bone and the bone plate are not perpendicular to the longitudinal axis of the bone plate. This is because the seat-engaging surface of the head of the screw and that of the lock washer fit on the whole contact area in these cases, too.

The lock washer can be employed with the following indications:

a. With osteoporotic bones or bones with a thin corticalis (since a rigid fixation is present between the plate and screw, a premature loosening, as can take place through cyclic loading, can be avoided);

b. With a bone defect in the superficial corticalis, as can appear for example with a comminuted fracture in the bone.

c. With any indications of former "blade plates", thus simplifying the whole instrumentation.

DESCRIPTION OF THE DRAWINGS

The specifics of the invention will be further explained with the help of drawings which depict the preferred design versions.

In the drawings.

DETAILED DESCRIPTION OF PREFERRED EMBODIMENTS

Figure 1:
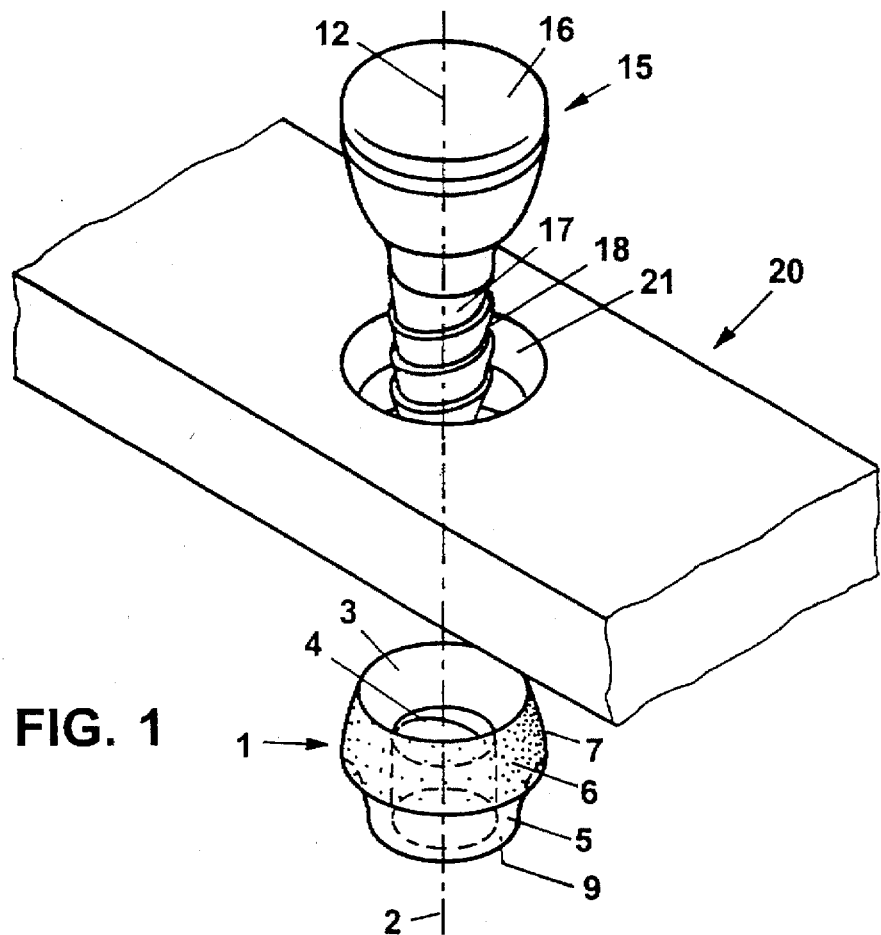
FIG. 1 shows an exploded perspective view of a bone plate with a bone screw and a locking washer according to the invention.
Figure 2:
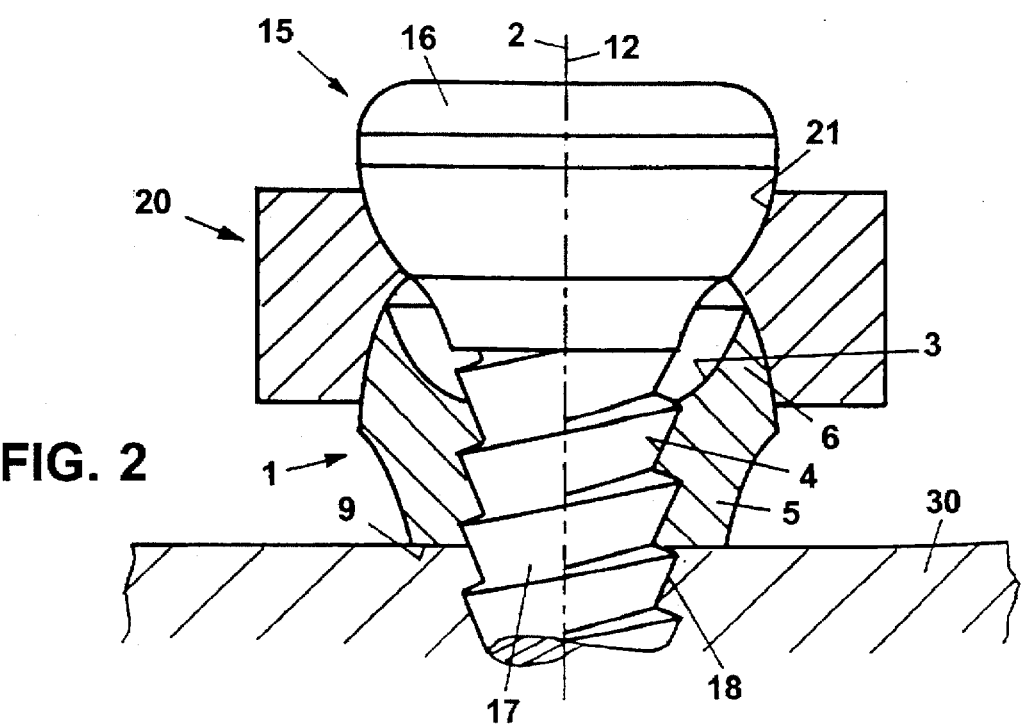
FIG. 2 shows a cross section perpendicular to the plate longitudinal axis through the bone plate with an inserted bone screw and a lock washer as in FIG. 1.

As depicted in FIGS. 1 and 2, in essence the lock washer 1 according to the invention consists of a one-piece foundation 5, 6 with a central axis 2, a central borehole 3 with an interior thread 4 to match exterior thread 18 of the bone screw 15, a lower section 5, an upper section 6 and a surface 9 adjoining bone 30.

Upper section 6 is formed in such a way that from below it can be inserted into borehole 21 in an essentially form-locking manner. Since borehole 21 curvedly tapers conically from below upwardly, upper section 6 is likewise configured as a curvedly tapered cone. Surface 7 of section 6 has been roughened so that with tightening of lock washer 1 at a point remote from the bone, a firm rotational stability within borehole 21 is achieved.

The average width of lower section 5 is smaller than the average width of upper section 6. This configuration is of great importance, since thereby a relatively small contact surface 9 on the bone is produced.

Upon screwing the shaft 17 of bone screw 15 into bone 30, the screw head 16, as depicted in FIG. 2, comes into proximity to, but does not touch lock washer 1, which is essential for the latter's function.

Figure 3:
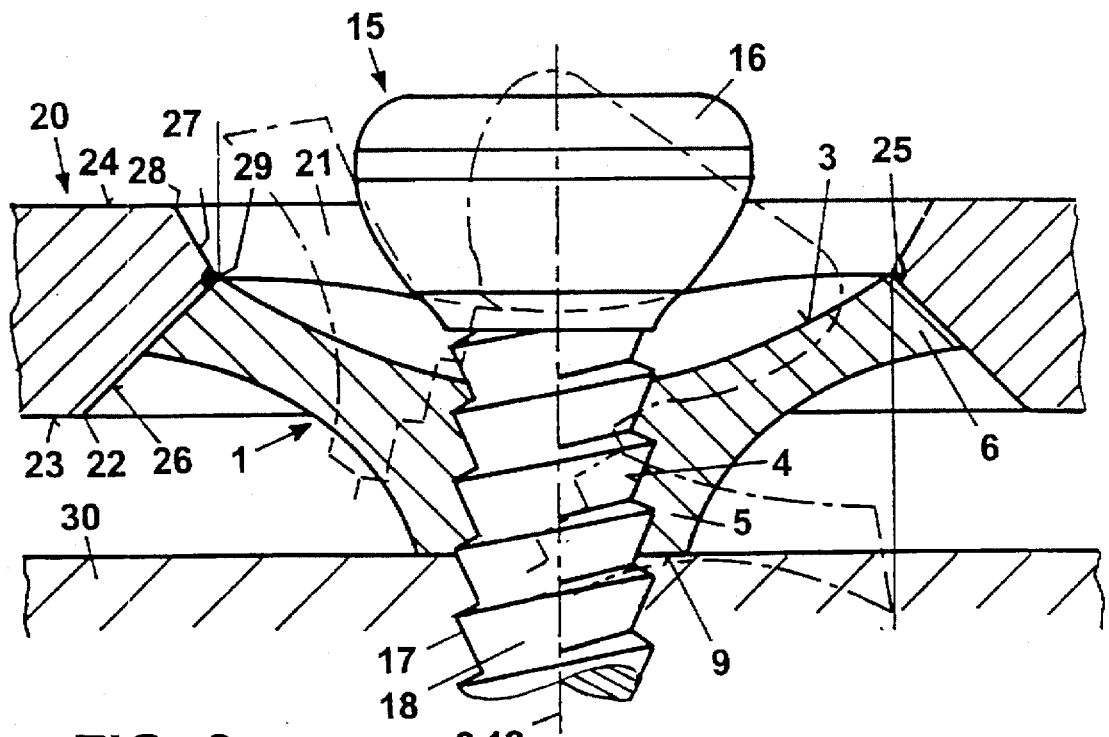
FIG. 3 shows a longitudinal section through a bone plate with an inserted bone screw and a version of the lock washer according to the invention.
Figure 4:
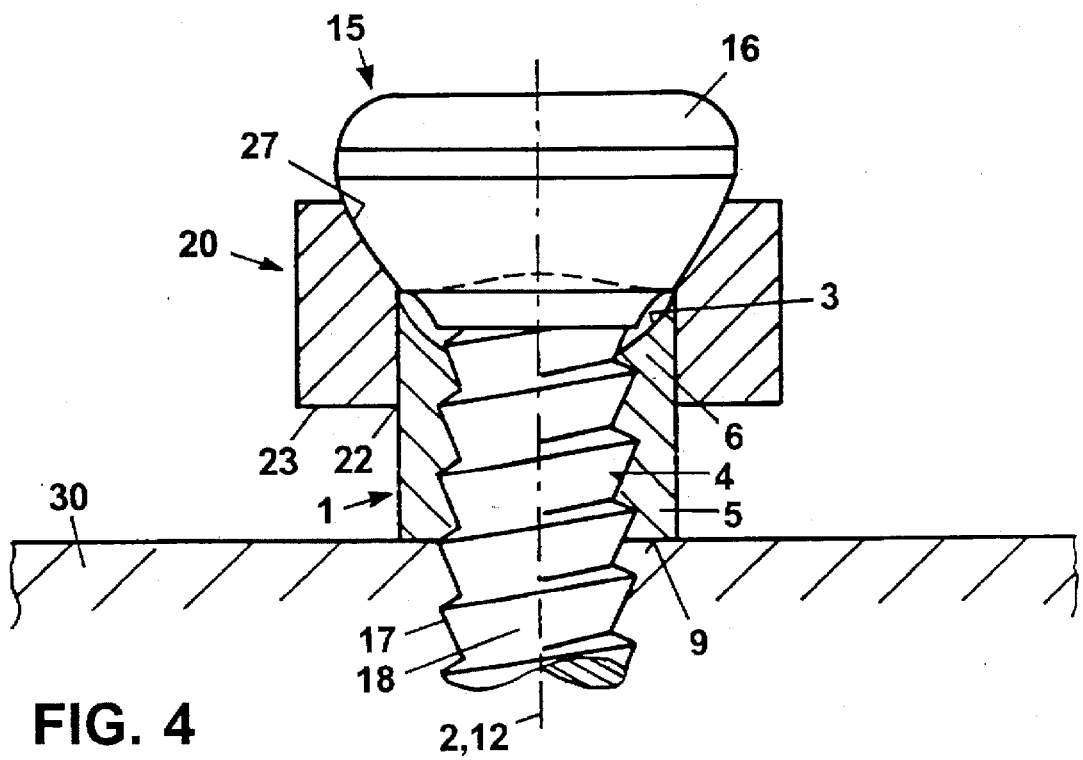
FIG. 4 shows a cross section perpendicular to the plate longitudinal axis through the bone plate with an inserted bone screw and a lock washer as in FIG. 3.
Figure 5:
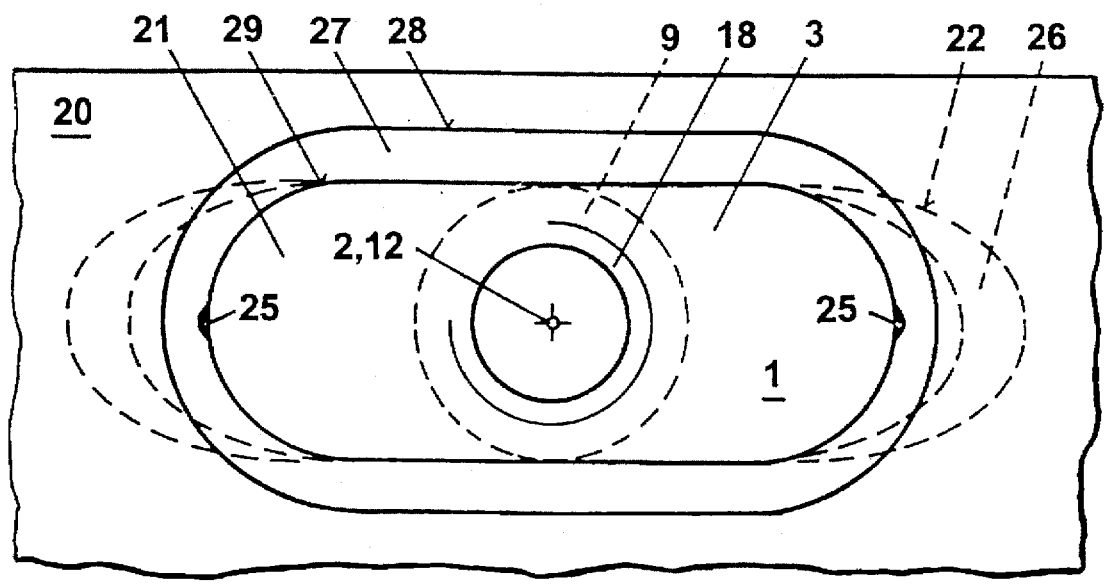
FIG. 5 shows a downward view of a bone plate with an inserted bone screw and a lock washer per FIG. 3.

In FIGS. 3–5 a version of lock washer 1 is depicted which has been adapted to the requirements for a bone plate 20 with a borehole 21 that is lengthened in the longitudinal direction of bone plate 20.

Locking disk 1 in this design configuration is no longer rotationally symmetrical, as in the configuration of FIGS. 1 and 2, but is elliptically configured, to adapt to the essentially oval geometry of borehole 21. As will appear from FIG. 5, the surface geometry of upper section 6 of lock washer 1 does not exactly match the edge 22 of borehole 21 on the underside 23 of bone plate 20, but rather is undersized in relation to it. This makes it possible to insert lock washer 1 not only from the underside 23 of bone plate 20 into borehole 21, but also from the upper side of borehole 21, which most appropriately takes place in such a way that lock washer 1 is temporarily screwed onto bone screw 15, and with the aid of the screw is inserted through borehole 21. For this purpose, axis 2 of lock washer 1 is inclined somewhat in the longitudinal direction of bone plate 20 (see the dashed outlines in FIG. 3) until it can be pressed downward via elastic nipples (or beads) 25, and then following straightening of axis 2 again in borehole 21 it can be drawn back and brought into proximity against the tapered conical section 26 of borehole 21. The nipples 25 are situated on two opposite sides in the longitudinal direction of borehole 21, specifically at the site of borehole 21 with the smallest width 29. Borehole 21 widens upwards from this smallest width 29 once again in a conical section 27 to the edge 28 of borehole 21 on the upper side 24 of bone plate 20.

The function of nipples 25, following the pulling back in the direction away from the bone described above, is to tightly jam lock washer 1 temporarily, so that lock washer 1 also does not fall out of borehole 21 if bone screw 15 is removed intraoperatively.

Figure 6:
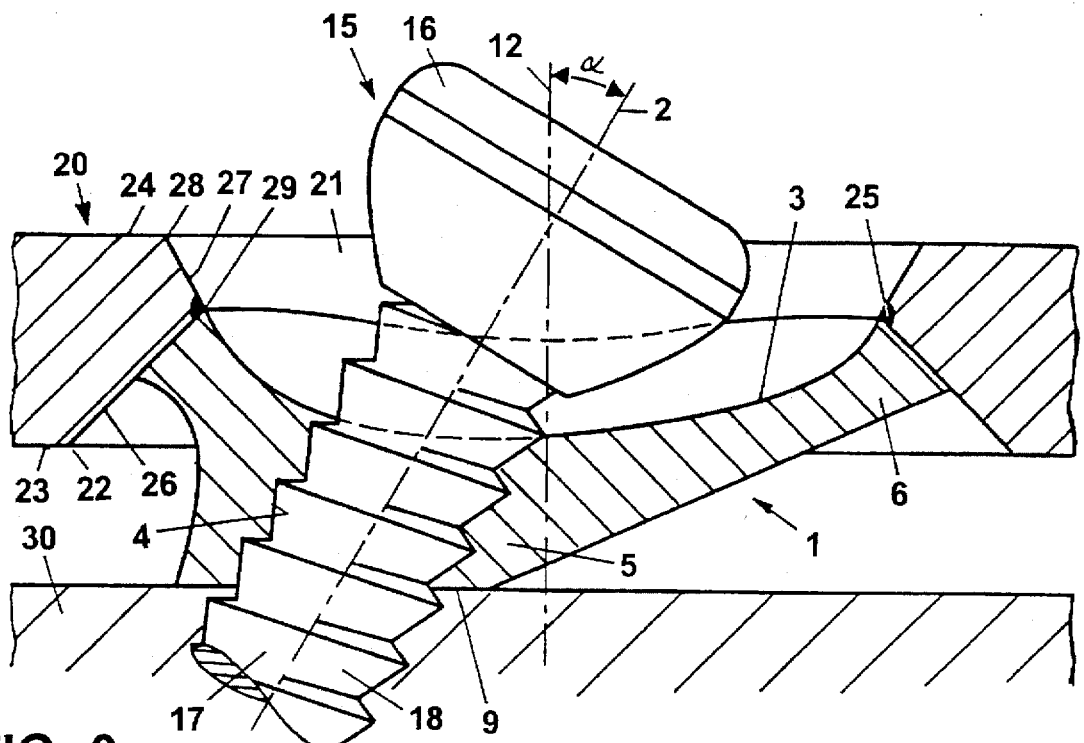
FIG. 6 shows a longitudinal section through a modified lock washer according to the invention for an angled bone screw.

FIG. 6 is a depiction of yet another version of the lock washer which permits a tilting of axis 2 of bone screw 15 relative to axis 12 of the borehole 21, here likewise configured as a longitudinal aperture. For this purpose, lock washer 1 is configured not merely to be oval, but also asymmetric, so that with proximity against the tapering conical section 26 of borehole 21, a tilt of bone screw at angle α results, which can be up to 30°. With this configuration nipples (or beads) 25 are provided which prevent lock washer 1, prior to locking, from falling out of borehole 21.

Figure 7:
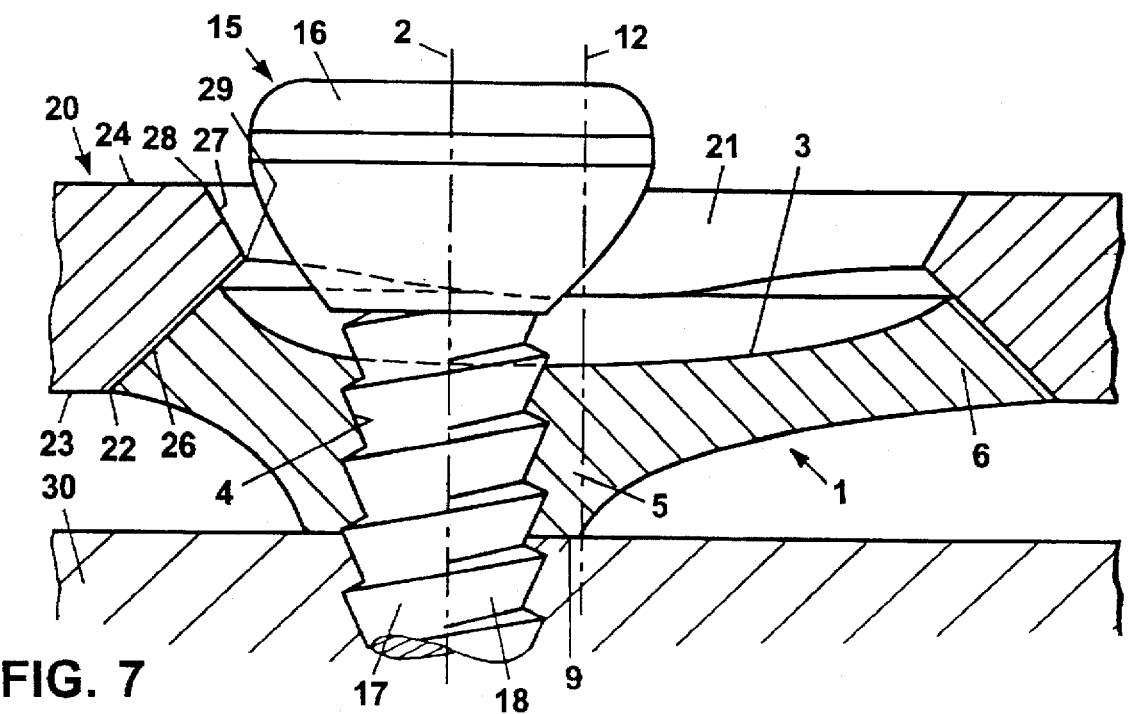
FIG. 7 shows a longitudinal section through a further modification of the lock washer according to the invention.

In FIG. 7 is a depiction of still another design configuration of lock washer 1, which has been modified for a bone plate 20 in which at least one of the boreholes 21 was formed as a so-called camming or glide hole. Bone screw 15 is therefore made to rest eccentrically in borehole 21. Also, borehole 3 is situated eccentrically in lock washer 1. The principle of such a glide hole is described in detail in Swiss patent CH-A5 650 915 to Klaue. In other respects lock washer 1 is configured similar to the above-described design configurations.

Finally, the camming effect can be used for the screw head as well as the lock washer simultaneously. The boring hole is drilled eccentrically in relation to the plate hole (oval). The lock washer is elongated but symmetrical. By tightening the screw, the screw head contacts the upper slope of the plate hole and produces the known "self-correcting effect". This action is completed by the lock washer which contacts the oblique undercut of the plate hole and produces a camming effect against the plate by being tightened against the screw head.

What is claimed is:

1. Lock washer for use in attaching a bone screw to a bone plate having a bore hole, said washer comprising a substantially cylindrical body having a central axis, a bore hole having internal threading for receiving a bone screw, a lower section having a surface adapted to abut the surface of a bone and an upper section, wherein the upper section is shaped to be retained in the plate bore hole and is curvedly tapered to form a surface shaped to engage a corresponding surface in the plate bore hole, and the lower section is smaller in average width than the upper section.

2. The lock washer claimed in claim 1 wherein the internal threading is in the lower section.

3. The lock washer claimed in claim 1 wherein the body tapers down from the upper section to the lower section.

4. The lock washer claimed in claim 1 wherein the upper section surface which engages the surface in the plate bore hole is roughened.

5. The lock washer claimed in claim 1 wherein the surface adapted to contact the surface of a bone is of lesser area than the area of a cross section of the upper section, perpendicular to the central axis.

6. An osteosynthetic fixation system comprising a bone plate having an upper surface, a lower surface for positioning to face a bone, and a plate bore hole extending from said upper surface to said lower surface, in combination with a lock washer having a body having a bore hole with internal threading for receiving a bone screw, a lower section having a surface adapted to abut the surface of a bone and an upper section, said upper section being curvedly tapered to form a surface shaped to engage a corresponding surface in the plate bore hole from said lower surface, said lower section being smaller in average width than said upper section.

7. The system claimed in claim 6 wherein the upper section is seated in the plate bore hole adjacent the lower surface of the plate.

8. The system claimed in claim 6 wherein the plate bore hole and the upper section are shaped to prevent rotation of the washer when inserted in the plate bore hole.

9. The system claimed in claim 6 wherein the washer bore hole, when the washer is seated in the plate bore hole, is coaxial with the plate bore hole.

10. The system claimed in claim 6 wherein the plate bore hole narrows between the upper and lower plate surfaces.

11. An osteosynthetic fixation system comprising a bone plate having an upper surface, a lower surface for positioning to face a bone, and a plate bore hole extending from said upper surface to said lower surface, in combination with a lock washer having a body having a bore hole with internal threading for receiving a bone screw, a lower section having a surface adapted to abut the surface of a bone and an upper section, said upper section being adapted for insertion in the plate bore hold from said lower surface, said lower section being smaller in average width than said upper section, wherein the body has an asymmetric configuration with respect to a transverse plane through and including the central axis of the washer bore hole, so that when the upper section is inserted in the plate bore hole, the axis of the washer bore hole forms an angle with the axis of the plate bore hole.

12. Bone fixation device comprising a bone plate having an upper surface, a lower surface, and a bore hole, a bone screw and a lock washer, said lock washer having a body with an upper section and a lower section wherein the upper section is curvedly tapered to form a surface shaped to engage a corresponding surface in the plate bore hole and the lower section is smaller in average width than the upper section and has a surface adapted to abut the surface of a bone.

13. The fixation device claimed in claim 12 wherein the plate bore hole has a shape widening toward the lower plate surface and the upper section of said lock washer has an upper section congruent with said plate bore hole.

14. The fixation device claimed in claim 13 wherein the surface of the plate bore hole is roughened.

15. An osteosynthetic fixation system comprising a bone plate having an upper surface, a lower surface for positioning to face a bone, and a plate bore hole extending from said upper surface to said lower surface, in combination with a lock washer having a body having a bore hole with internal threading for receiving a bone screw, a lower section having a surface adapted to abut the surface of a bone and an upper section, said upper section being adapted for insertion in the plate bore hole from said lower surface, said lower section being smaller in average width than said upper section, wherein the plate bore hole narrows between the upper and lower plate surfaces and at its narrowest point has securing elements for retaining the lock washer.

16. The system claimed in claim 15 wherein the securing elements are elastic nipples.

* * * * *